(12) United States Patent
Xia et al.

(10) Patent No.: US 7,659,259 B2
(45) Date of Patent: Feb. 9, 2010

(54) METHOD OF TREATING INFLAMMATION OF THE EYE

(75) Inventors: Erning Xia, Penfield, NY (US); Dharmendra M. Jani, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 7 days.

(21) Appl. No.: 11/955,418

(22) Filed: Dec. 13, 2007

(65) Prior Publication Data

US 2008/0153776 A1 Jun. 26, 2008

Related U.S. Application Data

(60) Provisional application No. 60/871,353, filed on Dec. 21, 2006.

(51) Int. Cl.
*A61K 31/734* (2006.01)
*A61K 31/715* (2006.01)

(52) U.S. Cl. .............. 514/54; 514/53; 514/61; 514/914; 536/123.1; 536/123.13

(58) Field of Classification Search .............. 514/54, 514/53, 61, 914; 536/123.1, 123.13
See application file for complete search history.

(56) References Cited

U.S. PATENT DOCUMENTS

| 5,776,445 A | 7/1998 | Cohen et al. |
| 6,399,605 B1 | 6/2002 | Maurin et al. |
| 2003/0232089 A1 | 12/2003 | Singh et al. |
| 2007/0004672 A1 | 1/2007 | Jani et al. |

FOREIGN PATENT DOCUMENTS

WO    WO 2005/082333 A1    9/2005

OTHER PUBLICATIONS

Mirshafiey et al., "Sodium Alginate as a Novel Therapeutic Option in Experimental Colitis," Scand. J. of Immun., 2005, (vol. 61), (p. 316-321).
Haug et al., "A Study of the Constitution of Alginic Acid by Partial Acid Hydrolysis," Acta Chemica Scand., 1966, (vol. 20), (Issue. 1), (p. 183-190).
Klock et al., "Biocompatibility of Mannuronic Acid-Rich Alginates," Biomaterials, 1997, (vol. 18), (p. 707-713).

*Primary Examiner*—Shaojia Anna Jiang
*Assistant Examiner*—Michael C Henry
(74) *Attorney, Agent, or Firm*—Toan P. Vo

(57) ABSTRACT

The present invention includes a method of treating inflammation of the eye comprising administering to an eye of a patient suffering from inflammation of the eye, a composition comprising an aqueous solution of alginate having a minimum of about 50% mannuronate residues based upon the total number of saccharide monomeric units.

16 Claims, No Drawings

METHOD OF TREATING INFLAMMATION OF THE EYE

CROSS-REFERENCE

This application claims the benefit of Provisional Patent Application No. 60/871,353 filed Dec. 21, 2006, which is incorporated by reference herein.

FIELD OF THE INVENTION

This invention relates to a composition for treating inflammation of the eye and a related method of use and method of manufacture. In particular, the invention relates to a method of treating inflammation of the eye without an active pharmaceutical agent.

BACKGROUND

Allergy is characterised by a local or systemic inflammatory response to allergens. Allergic conjunctivitis is a disorder that is characterized by the clinical signs and symptoms of eye itching, redness, tearing, and swelling. An estimated 20% of the population in the United States suffer from inflammation of the eye. The signs and symptoms of allergic conjunctivitis can significantly impact the quality of life of patients, from social interactions, productivity at work and school, to the ability to perform visual tasks such as working on a computer or reading.

Currently, available pharmaceutical treatments for inflammation of the eye or symptoms of inflammation of the eye include (1) antihistamines, (2) drugs that block the release of histamine and other substances from the mast cell (e.g., mast cell stabilizers), (3) drugs with multiple modes of action (e.g. antihistamine/mast cell stabilizing agents), and (4) drugs that can actively constrict blood vessels thus reducing redness and swelling (e.g., vasoconstrictors). Additionally, artificial tears have been used to wash the eye of allergens.

The desirability of a particular treatment for inflammation of the eye can be measured against the following factors (1) efficacy at onset of action, (2) duration of action, (3) efficacy at controlling signs and symptoms of allergic conjunctivitis, and (4) comfort of the drop when instilled in the eye.

Many patients desire an effective treatment by ingredients that are from natural sources and prefer treatment that avoids or reduces the amount of traditional active pharmaceutical ingredients used.

Alginate, for the purpose of this application is a polysaccharide that comprises β-D-mannuronic acid and α-L-guluronic acid monomers or salts or derivatives of such acids or salts.

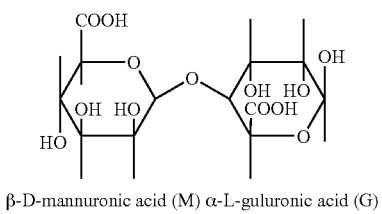

β-D-mannuronic acid (M) α-L-guluronic acid (G)

Some alginate polymers are block copolymers with blocks of the guluronic acid (or salt) monomers alternating with blocks of the mannuronic acid (or salt) monomers. Some alginate molecules have single monomers of guluronic acid (or salt) alternating with the comonomers of mannuronic acid (or salt). The ratio and distribution of the M and G components along with the average molecular weight affect the physical and chemical properties of the copolymer. See Haug, A. et al., *Acta Chem. Scand.* Vol. 20, 183-190 (1966). Alginate polymers have viscoelastic Theological properties and other properties that make it suitable for some medical applications. See Klock, G. et al., "Biocompatibility of manuronic acid-rich alginates," *Biomaterials*, Vol. 18, No. 10, 707-713 (1997).

The use of alginate as a thickener for topical ophthalmic use is disclosed in U.S. Pat. No. 6,399,605 and U.S. Patent Application Publication 2003/0232089 incorporated herein by reference in their entirety. In U.S. Pat. No. 5,776,445, alginate is used as a drug delivery agent that is topically applied to the eye. Particularly, the amount of guluronic acid in the alginate was taught to exceed 50%.

U.S. Patent Application Publication No. 2003/0232089 teaches a dry-eye formulation that contains two polymer ingredients including alginate.

WO2005/082333 discloses the use of sodium alginate in a viscoelastic formulation for ophthalmic surgery.

U.S. patent application Ser. No. 11/475,277 filed Jul. 1, 2005 teaches a dry eye formulation comprising alginate and a polyol. The alginate formulation contained certain ranges of Mannuronic:Guluronic ratios that were considered preferable.

Mirshafiey, et al., "Sodium alginate as a novel therapeutic option in the experimental colitis," Scand. J. Immunol., Vol. 61, 316-321 (2005) establishes that alginate inhibits cytokine, MMP2 and eicosanoid activity in a rat model suggesting that alginate could be useful to reduce inflammation in the colon of a rat.

In view of the above, it would be desirable to provide an eye-drop solution that will better alleviate the symptoms of inflammation of the eye and that is safe, convenient and economical to use. In particular, it would be highly desirable to develop a product having significantly greater duration of efficacy, in order to significantly decrease the number of times that the product may need to be administered to the eye, over the course of a day, in order to effectively treat the symptoms of inflammation of the eye. The present invention addresses these and other needs.

SUMMARY OF THE INVENTION

The present invention provides compositions and methods for treating inflammation of the eye caused by allergens. A method of the present invention includes administering to an eye of a patient suffering from inflammation of the eye, a composition comprising an aqueous solution of alginate. Alginate interacts with CD14 and TLR2 receptors on phagocytic cells, and inhibits production of inflammatory cytokines TNFα, IL-1, and IL-6 that are present in early immune response. Alginate triggers an immune response primarily in the non-specific immune system. In one aspect, the alginate has a minimum of about 50% mannuronate residues based upon the total number of saccharide monomeric units.

Typically, the alginate is formulated in an ophthalmically acceptable vehicle.

In one embodiment, the alginate is selected from the group consisting of *Laminaria digitata, Lessonia nigrescens, Macrocystis pyrifeira, Ascophyllum nodosum, Laminaria japonica,* and *Durvillea* species.

In another embodiment, the alginate has a minimum of about 70% mannuronate monomer units based upon the total number of monomer units.

In one embodiment, the composition further comprises a polyol. In another embodiment, the polyol contains 2 to 6 carbon atoms. Typically, the polyol may be sorbitol, xylitol, mannitol, glycerin, propylene glycol or a combination of these.

In another embodiment, the composition has a viscosity that is a maximum of about 30 cps.

In still another embodiment, the average molecular weight of alginate is a minimum of about 500 Da and a maximum of about 5000 kDa.

Preferably, the concentration of alginate in the composition is at a minimum of about 0.01 wt. % and a maximum of about 5 wt. % based upon the total weight of the composition.

In still another embodiment, the composition contains a polyol that is selected from the group consisting of glycerin, ethylene glycol, poly(ethylene glycol), propylene glycol, sorbitol, manitol and monosaccarides, disaccharides, neutral polysaccharides and oligosaccharides.

DETAILED DESCRIPTION OF THE INVENTION

The present invention provides compositions and methods for treating inflammation of the eye. The method includes administering to an eye of a patient suffering from inflammation of the eye, a composition comprising an aqueous solution of alginate.

As used herein mannuronate includes mannuronate in any salt form or its acid form—mannuronic acid.

Without being limited to a particular theory of operation, Applicant notes that alginate interacts with CD14 and TLR2 receptors on phagocytic cells, and induce production of inflammatory cytokines TNFα, IL-1, and IL-6 that are present in early immune response. In one embodiment, it is believed that higher mannuronate alginate may trigger an immune response primarily in the non-specific immune system.

In one embodiment the alginate has a minimum of about 50 wt. %, about 51 wt. %, about 59 wt. %, about 60 wt. %, about 70 wt. %, about 80 wt. %, about 85 wt. % or about 90 wt. % mannuronate residues based upon the total number of saccharide monomeric units in the alginate molecule.

In another embodiment, the alginate is selected from the group consisting of alginate purified from the following seaweed sources:

TABLE 1

Seaweed Raw Materials

| Source | Guluronate (%) | Mannuronate (%) |
|---|---|---|
| *Laminaria hyperborea* (stem) | 70 | 30 |
| *Lessonia trabeculate* | 67 | 33 |
| *Laminaria hyperborean* (whole plant) | 64 | 36 |
| *Laminaria hyperborean* (leaf) | 55 | 45 |
| *Laminaria digitata* | 41 | 59 |
| *Lessonia nigrescens* | 40 | 60 |
| *Macrocystis pyrifeira* | 39 | 61 |
| *Ascophyllum nodosum* | 36 | 64 |
| *Laminaria japonica* | 34 | 66 |
| *Durvillea* species | 31 | 69 |

The alginate of one embodiment is from the *Durvillea* species.

In another embodiment, the present invention includes the use of other mannuronate containing polysaccharide that have a mannuronate content greater than 50 wt. % based upon the total number of saccharide monomeric units in the polysaccharide in the method of the present invention.

Thus, in one embodiment, the present invention includes administering to an eye of a patient suffering from inflammation of the eye, a composition comprising an aqueous solution of a mannuronate containing polysaccharide having a minimum of about 50% mannuronate residues based upon the total number of saccharide monomeric units in the polysaccharide.

The various alginate products are available from commercial sources available to a person of ordinary skill in the art including FMC Corporation, Philadelphia, Pa.

The alginate of one embodiment has a molecular weight that is a minimum of about 50 kDa, about 80 kDa, about 100 kDa, about 500 kDa and/or a maximum of about 5000 kDa, about 2000 kDa, about 1000 kDa, about 700 kDa, about 500 kDa, about 200 kDa, about 100 kDa with ophthalmically pure polyol. In one preferred embodiment, the molecular weight is about 325 kDa.

The concentration of alginate is a minimum of about 0.01 wt. % and a maximum of about 2.0 wt. % based upon the total weight of the solution. Typically, the concentration of alginate is a minimum of about 0.05 wt. %, about 0.1 wt. %, about 0.25%, about 0.5 wt. % or about 1 wt. % based upon the total weight of the solution. Typically, the concentration of alginate is a maximum is about 5 wt. %, about 3 wt. %, about 2 wt. %, about 1.5 wt. % and about 1.2 wt. % based upon the total weight of the solution. Preferably, the concentration of alginate is about 0.5 wt. % based upon the total weight of the solution.

In one embodiment, the present invention includes administering to an eye of a patient suffering from inflammation of the eye, a composition comprising an aqueous solution of mannuronate containing disaccharides, trisaccharides or oligosaccharides having a minimum of about 50% mannuronate residues based upon the total number of saccharide monomeric units in the disaccharides, trisaccharides or oligosaccharides.

In one embodiment, the present invention includes administering to an eye of a patient suffering from inflammation of the eye, a composition comprising an aqueous solution of mannuronate. Mannuronate is optionally present in the composition in an amount that is a minimum of about 25% and/or a maximum of about 100% based upon the total number of alginate monomers.

According to one embodiment, the present invention optionally includes a polyol. The ratio of mannuronate monomers, mannuronate containing disaccharides, trisaccharides oligosaccharides or polysaccharides to polyol is a minimum of about 1:20, about 1:4, about 1:3, about 1:2.5, about 1:2, about 1:1, about 2:3 or about 3:4 and/or a maximum of about 20:1. about 4:1, about 3:1, about 2.5:1, about 2:1, about 1:1, about 3:2 or about 4:3.

In one embodiment, the formulation comprises a polyol. Polyols are defined as any ophthalmically acceptable compound with two adjacent —OH groups, but do not include alginate. The polyol of one embodiment of the present invention is typically a polyol containing 2 to 6 carbon atoms. Preferably, the polyol contains 2 to 4 carbon atoms. The polyol of one embodiment is selected from the group consisting of glycerin, ethylene glycol, poly(ethylene glycol), propylene glycol, sorbitol, manitol and monosaccarides, disaccharides, oligosaccharides and neutral polysaccharide. In one preferred embodiment, the polyol is selected from the group consisting of glycerin, ethylene glycol, propylene glycol, sorbitol, mannitol and monosaccarides. In another preferred embodiment, the polyol is selected from the group comprising disaccharides, oligosaccharides and poly(ethylene glycol). In one preferred embodiment, the polyol is glycerin.

The concentration of polyol including glycerin is a minimum of about 0.01 wt. % about 0.05 wt. % about 0.1 wt. % or about 0.5 wt. %, about 1 wt. %, and/or a maximum of about 1.5 wt. %, about 2 wt. %, about 3 wt. %, about 4 wt. % or about 5 wt. % based upon the total weight of the composition.

In one embodiment the polyol is a combination of glycerin and propylene glycol. Typically, the ratio of glycerin to propylene glycol is a minimum of about 30:70, about 35:65, about 40:60, about 45:55. The ratio of glycerin to propylene glycol is a maximum of about 70:30, about 65:35, about 60:40, about 55:45. In one embodiment, the ratio of glycerin to propylene glycol is 1:1. In one embodiment, the concentration of glycerin is a minimum of about 0.1 wt. %, about 0.3 wt. %, about 0.4 wt. % or about 0.5 wt. % and/or a maximum of about 0.8 wt. %, 0.9 wt. %, about 1 wt. %, about 1.5 wt. %, about 2 wt. % or about 3 wt. % based upon the total weight of the composition. In one embodiment the concentration of propylene glycol is a minimum of about 0.1 wt. %, about 0.3 wt. %, about 0.4 wt. % or about 0.5 wt. % and/or a maximum of about 0.8 wt. %, 0.9 wt. %, about 1 wt. %, about 1.5 wt. %, about 2 wt. % or about 3 wt. % based upon the total weight of the composition.

The present composition may also contain a disinfecting amount or a preservative amount of an antimicrobial agent. Antimicrobial agents are defined as organic chemicals that derive their antimicrobial activity through a chemical or physiochemical interaction with the microbial organisms. These include sorbic acid, quarternary ammonium polymers and low and high molecular weight biguanides. For example, biguanides include the free bases or salts of alexidine, chlorhexidine, hexamethylene biguanides and their polymers, and combinations of the foregoing. The salts of alexidine and chlorhexidine can be either organic or inorganic and are typically gluconates, nitrates, acetates, phosphates, sulfates, halides and the like. A preferred polymeric biguanide is poly (hexamethylene biguanide) commercially available from Zeneca, Wilmington, Del. under the trademark Cosmocil™ CQ. Generally, the hexamethylene biguanide polymers, also referred to as poly(aminopropyl biguanide) (PAPB), have molecular weights of up to about 100 kDa. A particularly preferred preservative is alexidine.

If used in the subject solution, the antimicrobial agent should be used in an amount which will preserve or prevent the growth of the microorganism population in the formulations employed. Preferably, a preservative amount is that which will reduce the bacterial bioburden after 28 days each by 3 logs and prevents the growth of fungal bioburden by ±0.5 log. Typically, such agents are present in a minimum concentration of about 0.0001 wt. %, 0.0003 wt. % or 0.0005 wt. % and a maximum concentration of about 0.0005 wt. % or 0.001 wt. % or about 0.005 wt. % based upon the total weight of the composition.

In one embodiment, the preservative is a gentle preservative that is a combination of Alexidine and zinc cation. The Alexidine and zinc cation preservative work synergistically to preserve the solution, in one embodiment. In one embodiment the amount of Alexidine is a minimum of about 1 ppm, about 2 ppm, or about 2.5 ppm and/or a maximum of about 5 ppm, about 4 ppm or about 3.5 ppm. In another embodiment, the amount of zinc cation is a minimum of about 0.005 wt. %, about 0.01 wt. % or about 0.02 wt. % and a maximum of about 1 wt. %, 0.5 wt. %, or 0.1 wt. % based upon the dry weight of zinc chloride. Optionally, the composition includes a magnesium cation. The amount of magnesium cation is a minimum of about 0.005 wt. %, about 0.01 wt. % or about 0.02 wt. % and a maximum of about 1 wt. %, 0.5 wt. %, or 0.1 wt. % based upon the dry weight of magnesium chloride.

The aqueous solutions employed in this invention may contain additional ingredients described above, one or more other components that are commonly present in ophthalmic solutions, for example, buffers, stabilizers, tonicity agents and the like, which aid in making ophthalmic compositions more comfortable to the user. The aqueous solutions of the present invention are typically adjusted with tonicity agents to approximate the tonicity of normal lacrimal fluids which is equivalent to a 0.9 wt. % solution of sodium chloride or a 2.8 wt. % of glycerol solution. The solutions are made substantially isotonic with physiological saline used alone or in combination. In some embodiment, the solutions may be desirably made hypotonic.

Correspondingly, excess salt or other tonicity agents may result in the formation of a hypertonic solution that will cause stinging and eye irritation. An osmolality is a minimum of about 200 mOsm/kg, about 225 mOsm/kg, about 250 mOsm/kg, about 260 mOsm/kg, about 280 mOsm/kg, about 300 mOsm/kg or about 320 mOsm/kg and/or a maximum of about 400 mOsm/kg, about 380 mOsm/kg, about 360 mOsm/kg, about 340 mOsm/kg or about 320 mOsm/kg. Most preferably, the osmolality is in the range from about 240 mOsm/kg to about 320 mOsm/kg.

Preferably, the composition of at least one embodiment of the present invention has a low ionic strength. Typically, the composition contains low concentration of mono or divalent cations typically found in tear fluids. Generally, the composition contains a low concentration of one or more of the following cations: Na+, K+, Ca++, Mg++, and Zn++. In one embodiment, the concentration of the mono or divalent cations that are typically found in tear fluids (i.e. Na+, K+, Ca++, Mg++ and Zn++) has a minimum concentration of about 0.001 wt. %, about 0.005 wt. %, about 0.01 wt. % or about 0.1 wt. % and/or a maximum of about 0.1 wt. %, about 0.01 wt. %, about 0.1 wt. %, about 0.05 wt. % or about 0.01 wt. % based upon the total weight of the composition.

The pH of the present solutions used to treat inflammation of the eye should be maintained at a minimum of about 4 about 5, about 5.5, about 6, about 6.5 and/or a maximum of about 7.5, about 7.8, about 8, about 8.5. Suitable buffers may be added, such as borate, citrate, bicarbonate, aminoalcohol buffers, MOPS buffer, bicine, tricine, TRIS, BIS/TRIS and various mixed phosphate buffers (including combinations of $Na_2HPO_4$, $NaH_2PO_4$ and $KH_2PO_4$) and mixtures thereof. Preferred combination buffers include borate/phosphate and borate/citrate combination buffers. Generally, buffers will be used in amounts having a minimum of about 0.05 wt. % or about 0.1 wt. % and/or a maximum of about 1.5 wt. % or about 2.5 wt. %.

In addition to buffering agents, in some instances it may be desirable to include sequestering agents in the present solutions in order to bind metal ions, which might otherwise react with the lens and/or protein deposits and collect on the lens. Ethylene-diaminetetraacetic acid (EDTA) and its salts (disodium) are preferred examples. They are usually added in amounts having a minimum of about 0.01 wt. % and/or a maximum of about 0.2 wt. %.

The present invention includes a method of treating inflammation of the eye comprising administering to an eye a composition comprising an aqueous solution of alginate and a polyol to the eye. In one embodiment, the composition does not have, or is free of, an active pharmaceutical agent. In one aspect, a composition of the present invention comprises alginate and is free of active pharmaceutical agents other than anti-inflammatory agents. The method further includes administering to an eye a composition to any one or more embodiments or combination of embodiments disclosed herein.

The composition may optionally include an anti-inflammatory agent including coricosteroids or other steroid compounds. Examples of known corticosteroids include dexamethasone, loteprednol etabonate, etc. Other steroidal compounds such as prednisolone and related compounds and low solubility steroids such as fluocinolone acetonide and related compounds are envisioned as being within the content of the invention disclosed herein. Other anti-inflammatories such as hydrocortisone, hydrocortisone acetate, dexamethasone 21-phosphate, fluocinolone, medrysone, methylprednisolone, prednisolone 21-phosphate, prednisolone acetate, fluorometholone, betamethasone and triamcinolone. Typical concentrations of antiinflammatories and steroids in the final formulation may range from 0.01 to 2.0 percent by weight.

In one embodiment, there is a method of manufacturing a composition for treatment of inflammation of the eye. The method of manufacturing comprises combining in an aqueous solution ophthalmically pure alginate (or optionally mannuronate monomers, mannuronate containing disaccharides, trisaccharides oligosaccharides or polysaccharides). In one embodiment, the mannuronate containing disaccharides, trisaccharides, oligosaccharides or polysaccharides are selected to have a minimum of about 50% mannuronate monomers as a percentage of the total number of monomeric units.

As indicated above, the present invention is useful for treating inflammation of the eye, or, more specifically, its symptoms. For that purpose, compositions for use in the present invention may be sold in a wide range of small-volume containers from 1 ml to 30 ml in size. Such containers can be made from HDPE (high density polyethylene), LDPE (low density polyethylene), polypropylene, poly(ethylene terephthalate) and the like. Flexible bottles having conventional eye-drop dispensing tops are especially suitable for use with the present invention.

The above-described solutions, in accordance with the present invention, may be used by instilling, for example, about one (1) or three (3) drops in the affected eye(s) as needed, for the temporary relief of inflammation of the eye.

EXAMPLE 1

The following ingredients listed in Table 2 and respective amounts are used to make a base formulation with different alginate sources having different Mannuronic to Guluronic ratios:

TABLE 2

Formula 1

| Base Formulation | mg/g | % w/w |
|---|---|---|
| Boric Acid | 5 | 0.5 |
| Sodium Borate | 0.14 | 0.014 |
| Glycerin | 6 | 0.6 |
| Propylene Glycol | 6 | 0.6 |
| Alginate (*Durvellea* species) | 2.5 | 0.25 |
| HAP (30%) | 0.5 | 0.05 |
| Alexidine 2HCl | 3 ppm | 3 ppm |
| Purified Water | Q.S. to 1000 mg | Q.S. to 100% w/w |

Formulation Process: A volume of purified water that is equivalent to from about 85% to about 90% of the total batch weight (the temperature of purified water should be below 40° C. before add any raw material) is added into an appropriate stainless steel mixing vessel. Preferably, the temperature of the purified water should be below 40° C. during this step. Alginate is selected from the *Durvellea* species. Furthermore, the alginate preferably has an average molecular weight of about 325 kDa. Alginate is added slowly with continued agitation and mixed thereafter for at least 45 minutes.

After the addition of Alginate and corresponding mixing, the following ingredients are slowly added in the order listed and mixed for at least 30 minutes:

Boric Acid

Sodium Borate

HAP (30%)

Glycerin

Propylene Glycol

After these ingredients are mixed, Alexidine HCl was added via a 0.22 μm sterilizing filter and mixed for an additional 30 minutes or more. The preparation is ready for packaging, use and storage. Refrigeration is not needed.

EXAMPLE 2

The following ingredients listed in Table 3 and respective amounts are used to make Formula 2:

TABLE 3

Formula 2

| Ingredients | mg/g | % w/w |
|---|---|---|
| Boric Acid | 5 | 0.5 |
| Sodium Borate | 0.14 | 0.014 |
| Glycerin | 6 | 0.6 |
| Propylene Glycol | 6 | 0.6 |
| Alginate (Medium Viscosity) | 2.5 | 0.25 |
| HAP (30%) | 0.5 | 0.05 |
| LE | 5 | 0.5 |
| Alexidine 2HCl | 3 ppm | 3 ppm |
| Purified Water | Q.S. to 1000 mg | Q.S. to 100% w/w |

EXAMPLE 3

The following ingredients listed in Table 4 and respective amounts are used to make Formula 3:

TABLE 4

Formula 3

| Ingredients | mg/g | % w/w |
|---|---|---|
| Boric Acid | 5 | 0.5 |
| Sodium Borate | 0.14 | 0.014 |
| Glycerin | 6 | 0.6 |
| Propylene Glycol | 6 | 0.6 |
| Alginate (Medium Viscosity) | 2.5 | 0.25 |
| HA | 2 | 0.2 |
| HAP (30%) | 0.5 | 0.05 |
| Alexidine 2HCl | 3 ppm | 3 ppm |
| Purified Water | Q.S. to 1000 mg | Q.S. to 100% w/w |

EXAMPLE 4

The following ingredients listed in Table 5 and respective amounts are used to make Formula 4:

TABLE 5

Formula 4

| Ingredients | mg/g | % w/w |
|---|---|---|
| Boric Acid | 5 | 0.5 |
| Sodium Borate | 0.14 | 0.014 |
| Glycerin | 6 | 0.6 |
| Propylene Glycol | 6 | 0.6 |
| Alginate (Medium Viscosity) | 2.5 | 0.25 |
| HA | 2 | 0.2 |
| HAP (30%) | 0.5 | 0.05 |
| LE | 3 | 0.3 |
| Alexidine 2HCl | 3 ppm | 3 ppm |
| Purified Water | Q.S. to 1000 mg | Q.S. to 100% w/w |

EXAMPLE 5

The following ingredients listed Table 6 and respective amounts are used to make Formula 5:

TABLE 6

Formula 5

| Ingredients | mg/g | % w/w |
|---|---|---|
| Boric Acid | 5 | 0.5 |
| Sodium Borate | 0.14 | 0.014 |
| Glycerin | 6 | 0.6 |
| Propylene Glycol | 6 | 0.6 |
| Alginate (Medium Viscosity) | 2.5 | 0.25 |
| HA | 2 | 0.2 |
| HAP (30%) | 0.5 | 0.05 |
| Loteprednol etabonate | 3 | 0.3 |
| Purified Water | Q.S. to 1000 mg | Q.S. to 100% w/w |

EXAMPLE 6

The following ingredients in Table 7 and respective amounts are used to make Formula 6:

TABLE 7

Formula 6

| Ingredients | mg/g | % w/w |
|---|---|---|
| Boric Acid | 5 | 0.5 |
| Sodium Borate | 0.14 | 0.014 |
| Glycerin | 6 | 0.6 |
| Propylene Glycol | 6 | 0.6 |
| Alginate (Medium Viscosity) | 2.5 | 0.25 |
| HA | 2 | 0.2 |
| HAP (30%) | 0.5 | 0.05 |
| LE | 3 | 0.3 |
| Zinc Chloride | 0.2 | 0.02 |
| Purified Water | Q.S. to 1000 mg | Q.S. to 100% w/w |

EXAMPLE 7

The following ingredients and respective amounts are used to make Formula 7 of the present invention:

TABLE 8

Formula 7

| Ingredient | mg/g | % w/w |
|---|---|---|
| Boric Acid | 5 | 0.5 |
| Sodium Borate | 0.14 | 0.014 |
| Glycerin | 6 | 0.6 |
| Propylene Glycol | 6 | 0.6 |
| Alginate (Medium Viscosity) | 2.5 | 0.25 |
| HA | 2 | 0.2 |
| HAP (30%) | 0.5 | 0.05 |
| Chondroitin Sulfate | 2 | 0.2 |
| LE | 3 | 0.3 |
| Alexidine 2HCl | 3 ppm | 3 ppm |
| Purified Water | Q.S. to 1000 mg | Q.S. to 100% w/w |

EXAMPLE 8

The following ingredients listed in Table 9 and respective amounts are used to make Formulations 8-10.

TABLE 9

| Ingredient | Formula 8 % (w/w) | Formula 9 % (w/w) | Formula 10 % (w/w) |
|---|---|---|---|
| Sodium Borate | 0.014 | 0.014 | 0.014 |
| Boric Acid | 0.5 | 0.5 | 0.5 |
| Glycerin | 0.6 | 0.6 | 0.6 |
| Propylene Glycol | 0.6 | 0.6 | 0.6 |
| Sodium Alginate | 0.25 | 0.25 | 0.25 |
| Zinc Chloride | 0.02 | 0.02 | — |
| Magnesium Chloride | 0.01 | 0.01 | — |
| Alexidine | — | 3 ppm | 3 ppm |

EXAMPLE 9

Test solutions, prepared in accordance with Formula 8-10, were tested for ISO/FDA microbial preservative efficacy using five FDA/ISO challenge microorganisms, i.e., three bacteria and two fungi. FDA recommended test organisms for preservative efficacy testing are composed of the following bacteria (*Pseudomonas aeruginosa* ATCC 9027, *Stapylococcus aureus* ATCC 6538, and *Escheria coli* ATCC 8739) and two fungi (*Candida albicans* ATCC 10231, and *Fusarium solani* ATCC 36031). Acceptance criteria established for bacteria require that the number of viable bacteria, recovered per ml is reduced by not less than 3.0 logs at 14 days. After the rechallenge at day 14, the concentration of bacteria shall be reduced by at least 3.0 logs by day 28. Acceptance criteria established for yeasts and molds require that the number of viable yeasts and molds, recovered per ml, remain at or below initial concentrations within an experimental error of ±0.5 logs within 14 days. After day 28, the concentration of mold and yeast shall remain at or below the concentrations after rechallenge within an experimental error of ±0.5 logs. Results are reported in Table 10.

TABLE 10

| | | | | |
|---|---|---|---|---|
| S. Aureus | 14 days | >4.8 | >4.8 | 4.8 |
| | 28 days | 3.5 | >3.8 | 3.6 |
| P. Aeruginosa | 14 days | 1.7 | 4.2 | 4.4 |
| | 28 days | 1.8 | 3.2 | >3.7 |
| E. Coli | 14 days | 4.7 | 4.4 | 4.5 |
| | 28 days | >3.7 | 3.3 | 1.7 |

TABLE 10-continued

| | | | | |
|---|---|---|---|---|
| C. Albicans | 14 days | 1.0 | 0.5 | 1.5 |
| | 28 days | 1.3 | 1.1 | 1.6 |
| A. Niger | 14 days | 2.0 | 2.0 | 2.0 |
| | 28 days | 1.4 | 1.2 | 0.8 |

EXAMPLE 10

The following ingredients listed in Table 11 and respective amounts are used to make Formulas 11-13.

TABLE 11

Formulas 11-13

| Ingredient | Formula 11 % (w/w) | Formula 12 % (w/w) | Formula 13 % (w/w) |
|---|---|---|---|
| Sodium Borate | 0.014 | 0.014 | 0.014 |
| Boric Acid | 0.5 | 0.5 | 0.5 |
| Glycerin | 0.6 | 0.6 | 0.6 |
| Propylene Glycol | 0.6 | 0.6 | 0.6 |
| Sodium Alginate | 0.25 | 0.25 | 0.25 |
| Zinc Chloride | 0.02 | 0.02 | — |
| Magnesium Chloride | 0.01 | 0.01 | — |
| Alexidine | — | 2 ppm | 2 ppm |

EXAMPLE 11

Test solutions, prepared in accordance with Formula 11-12, were tested for ISO/FDA microbial preservative efficacy using five FDA/ISO challenge microorganisms, i.e., three bacteria and two fungi according to the process of Example 9. The results are listed in Table 12 as follows:

TABLE 12

| | | | | |
|---|---|---|---|---|
| S. Aureus | 14 days | >4.8 | 4.0 | 4.3 |
| | 28 days | 3.5 | >3.8 | >3.8 |
| P. Aeruginosa | 14 days | 1.7 | 4.2 | 4.7 |
| | 28 days | 1.8 | 2.8 | 3.2 |
| E. Coli | 14 days | 4.7 | 4.3 | 4.7 |
| | 28 days | >3.7 | 3.2 | 1.8 |
| C. Albicans | 14 days | 1.0 | 0.5 | 1.2 |
| | 28 days | 1.3 | 1.0 | 1.4 |
| A. Niger | 14 days | 2.0 | 1.9 | 1.9 |
| | 28 days | 1.4 | 1.0 | 1.2 |

EXAMPLE 12

Treatment of Allergic Eye Condition

The formulation of Example 1 is administered to a group of patients that suffer from eye allergies. The administration of the drops appears to improve symptoms of inflammation of the eye. While not wishing to be bound by any particular theory, Applicant notes that the alginate interacts with CD14 and TLR2 receptors on phagocytic cells, and reduce production of inflammatory cytokines TNFα, IL-1, and IL-6 that are present in early immune response.

EXAMPLE 13

Prevention of Allergic Eye Condition

The formulation of Example 1 is administered to one of two populations of inflammation of the eye sufferers identified as the test population four times daily. The control population is provided with artificial tear solution and is administered four times daily during peak allergy season. The test population is expected to have fewer complaints than the control population.

While the invention has been described in conjunction with the detailed description and specific examples, this is illustrative only. Accordingly, many alternatives, modifications and variations will be apparent to those skilled in the art in light of the foregoing description and it is, therefore, intended to embrace all such alternatives, modifications and variations as to fall within the spirit and scope of the appended claims.

What is claimed is:

1. A method of treating inflammation of the eye comprising administering to an eye of a patient suffering from inflammation of the eye, a composition comprising an aqueous solution of alginate, wherein said aqueous solution is free of an active pharmaceutical agent, and wherein the alginate has a minimum of about 59 weight % mannuronate residues based upon a total number of saccharide monomeric units in the alginate molecule.

2. The method of claim 1, wherein the composition comprises an ophthalmically acceptable vehicle.

3. The method of claim 1, wherein the alginate is selected from the group consisting of *Laminaria digitata, Lessonia nigrescens, Macrocystis pyrifeira, Ascophyllum nodosum, Laminaria japonica*, and *Durvillea* species.

4. The method of claim 1, the composition further comprises a polyol.

5. The method of claim 1, the composition further comprises a polyol containing 2 to 4 carbon atoms.

6. The method of claim 1, the composition further comprises a polyol that is a combination of glycerin and propylene glycol.

7. The method of claim 1, wherein the composition has a viscosity that is a maximum of about 30 cps.

8. The method of claim 1, wherein the average molecular weight of alginate is a minimum of about 50 kDa and a maximum of about 5000 kDa.

9. The method of claim 1, wherein the alginate is present in the composition at a minimum of about 0.01 wt. % and a maximum of about 5 wt. % based upon the total weight of the composition.

10. The method of claim 1, wherein the composition further comprises a buffer selected from the group comprising phosphate buffer, borate buffer, MOPS buffer, citrate buffer, phosphate/borate buffer, citrate/borate buffer, an aminoalcohol buffer and combinations thereof.

11. The method of claim 1, wherein the composition has a pH in a range from about 4 and to about 8.

12. The method of claim 1, wherein the composition has a tonicity in a range from about 200 to about 400.

13. A method of treating allergic eye comprising administering to an eye a composition comprising a mannuronate-containing disaccharide, trisaccharide, oligosaccharide, or polysaccharide, wherein mannuronate units in the mannuronate-containing disaccharide, trisaccharide, oligosaccharide, or polysaccharide comprises a minimum of about 59% of the total number of saccharide monomeric units in the disaccharide, trisaccharide, oligosaccharide, or polysaccharide.

14. A method of improving symptoms of inflammation of the eye comprising administering to an eye of a patient suffering from inflammation of the eye, a composition comprising an aqueous solution of alginate, wherein said aqueous solution is free of an active pharmaceutical agent, wherein said symptoms are improved compared to an eye of a said patient who does not receive said composition, and wherein the alginate has a minimum of about 59 weight % mannuronate residues based upon a total number of saccharide monomeric units in the alginate molecule.

15. The method of claim 14, wherein said alginate comprises greater than 64% mannuronate units based upon a total number of saccharide monomeric units in the alginate molecule.

16. The method of claim 14, wherein said alginate comprises a minimum of 60% mannuronate units based upon a total number of saccharide monomeric units in the alginate molecule.

* * * * *